(12) United States Patent
Turnbow (10) Patent No.: US 11,471,344 B1
(45) Date of Patent: Oct. 18, 2022

(54) WHEELCHAIR HANDLE GRIP

(71) Applicant: Cody Turnbow, Capitan, NM (US)

(72) Inventor: Cody Turnbow, Capitan, NM (US)

( * ) Notice: Subject to any disclaimer, the term of this patent is extended or adjusted under 35 U.S.C. 154(b) by 767 days.

(21) Appl. No.: 16/406,185

(22) Filed: May 8, 2019

Related U.S. Application Data (60) Provisional application No. 62/818,460, filed on Mar. 14, 2019.

(51) Int. Cl.
*A61G 5/10* (2006.01)
*A61M 25/02* (2006.01)
*F16L 3/223* (2006.01)

(52) U.S. Cl.
CPC ......... *A61G 5/10* (2013.01); *A61M 2025/028* (2013.01); *B60Y 2200/84* (2013.01); *F16L 3/223* (2013.01)

(58) Field of Classification Search
CPC ............... A61G 5/10; A61M 2025/028; B60Y 2200/84; F16L 3/223; A45C 13/26; A45C 13/262; A45C 13/28; B65D 25/28; A45F 5/102; A45F 5/1026; A45F 2005/1033; A45F 2005/104; A45F 5/1046; A45F 2005/1053; A45F 2005/106
See application file for complete search history.

(56) References Cited

U.S. PATENT DOCUMENTS

| | | | | |
|---|---|---|---|---|
| 850,705 | A * | 4/1907 | Willis | A45F 5/1026 294/169 |
| 1,020,722 | A * | 3/1912 | Somerville | A45F 5/1026 294/169 |
| 1,081,559 | A * | 12/1913 | Somerville | A45F 5/1026 294/169 |
| 1,246,587 | A * | 11/1917 | Giardino | A45F 5/1026 294/169 |
| 2,876,486 | A | 7/1957 | Lindstrom | |
| 3,165,110 | A * | 1/1965 | Brooks | E04H 15/644 D25/120 |
| 5,044,650 | A | 9/1991 | Eberle, Jr. | |
| 5,703,330 | A * | 12/1997 | Kujawski | F16L 3/26 24/339 |
| 5,915,712 | A | 6/1999 | Stephenson et al. | |
| 7,841,355 | B2 * | 11/2010 | Livacich | E04H 15/30 135/120.3 |

(Continued)

FOREIGN PATENT DOCUMENTS

| | | |
|---|---|---|
| EP | 1 990 038 B1 | 10/2011 |
| JP | 2008-79768 A | 4/2008 |

OTHER PUBLICATIONS

Karman, "Hand Grips Parts—Wheelchair"; website offer for sale, https://www.karmanhealthcare.com/product/hand-grips/; available by Dec. 20, 2018, last visited Oct. 31, 2019.

(Continued)

*Primary Examiner* — Jacob D Knutson
*Assistant Examiner* — Conan D Duda
(74) *Attorney, Agent, or Firm* — Rod D. Baker (57) ABSTRACT

A handle grip specially adapted for installation and use upon the main push handles of a wheelchair. The handle grip is adapted to facilitate the reliable, yet temporary, attachment to the wheelchair push handles of the strap(s) and/or the oxygen tube(s) associated with an oxygen tank or generator source for supplying therapeutic oxygen gas to a patient seated in the wheelchair.

14 Claims, 5 Drawing Sheets

(56) References Cited

U.S. PATENT DOCUMENTS

| | | | |
|---|---|---|---|
| 8,678,418 B1 | 3/2014 | Quarles | |
| 2004/0118982 A1* | 6/2004 | Shillings | F16L 3/223 248/68.1 |
| 2004/0188570 A1* | 9/2004 | Bauer | F16L 55/035 248/68.1 |
| 2005/0077436 A1* | 4/2005 | Nelson | F16L 3/223 248/68.1 |
| 2007/0074917 A1* | 4/2007 | Jaenke | F16B 2/065 180/65.1 |
| 2008/0006317 A1* | 1/2008 | Livacich | E04H 15/44 135/123 |
| 2009/0044380 A1 | 2/2009 | Moore et al. | |
| 2010/0040307 A1* | 2/2010 | Lien | B65D 33/246 383/12 |
| 2011/0147542 A1* | 6/2011 | Hoek | H02G 3/32 248/68.1 |
| 2011/0210215 A1* | 9/2011 | Nitsche | F16L 3/24 248/74.1 |
| 2011/0232038 A1 | 9/2011 | Miller | |
| 2012/0277682 A1* | 11/2012 | Corato | F16L 3/26 604/179 |
| 2013/0175407 A1* | 7/2013 | Williams | F16L 3/223 248/68.1 |
| 2014/0035253 A1* | 2/2014 | Helterbrand | A61G 5/1083 280/250.1 |
| 2014/0259620 A1* | 9/2014 | Hicks | F16L 3/233 29/525.01 |
| 2015/0296949 A1* | 10/2015 | Pitchforth | A45F 5/1046 16/411 |
| 2015/0377387 A1* | 12/2015 | Meyers | F16L 3/22 425/130 |
| 2016/0096492 A1* | 4/2016 | Stau | F16L 3/227 248/632 |
| 2021/0161751 A1* | 6/2021 | Haddican | A61H 3/04 |
| 2021/0244904 A1* | 8/2021 | Perrie | A61M 16/0497 |

OTHER PUBLICATIONS

Cubro, "Cubro Handgrip to Suit Uribarri Wheelchair Range"; website offer for sale, https://cubro.co.nz/products/parts/handgrip-to-suit-uribarri-wheelchair-range-zz0520032; available by Dec. 20, 2018, last visited Oct. 31, 2019.

Magmedix, "MRI Wheelchair Push Handle Grip"; website offer for sale, http://www.magmedix.com/mri-wheelchair-push-handle-grip.html; available by Dec. 20, 2018, last visited Oct. 31, 2019.

Nithsdale, "Pair of Ergonomic Handgrips Nithh963"; website offer for sale, https://www.nithsdale-wheelchairs.com/prods/10853/pair-of-ergonomic-handgrips-nithh963.html; available by Dec. 20, 2018, last visited Oct. 31, 2019.

Spinlife, "6-inch Hand Grip for Invacare Manual Wheelchairs"; website offer for sale, https://www.spinlife.com/Invacare-6-Hand-Grip-for-Invacare-Manual-Wheelchairs-Hand-Grips/spec.cfm?productID=87272; available by Dec. 20, 2018, last visited Oct. 31, 2019.

* cited by examiner

WHEELCHAIR HANDLE GRIP

CROSS-REFERENCE TO RELATED APPLICATIONS

This application claims priority to and the benefit of the filing of U.S. Provisional Patent Application Serial No. 62/818,460 entitled "Wheelchair Handle Grip," filed 14 Mar. 2019, the entire disclosure of which is incorporated herein by reference.

BACKGROUND OF THE INVENTION

Field of the Invention

The invention relates generally to handlebar grips, particularly to handle grips for handles on wheelchairs.

Background of the Invention

There is provided according to this disclosure a hand grip specially adapted for installation and use upon the main push handles of a wheelchair. The main, or push, handles of a wheelchair are those that extend rearward from the upper portion of the wheelchair frame; there are conventionally two handles to be grasped by a person pushing and steering the wheelchair. Usually, of course, a non-ambulatory patient is seated in the wheelchair while a second person, herein a "caregiver," grasps a handle in each hand and therewith pushes/pulls and steers the wheelchair. The end of each wheelchair push handle ordinarily is provided with a grip, typically of molded flexible plastic, to improve the caregiver's grip and improve grasping comfort. Known grips are typically simply hollow cylinders with one open end and one closed end. The free end of a wheelchair handle is inserted into the open end of the grip, and the grip is slipped tightly over and along the handle until it is in proper place, usually when the end of the handle contacts the inside of the closed end of the grip. Known grips often, but not necessarily, have three or four low, relatively gently curved, bumps or ridges that extend downward from a properly installed grip and correspond to the recesses/depressions between the caregiver's fingers when gripping the grip.

Frequently, patients in wheelchairs receive oxygen gas ($O_2$) from a small oxygen tank or oxygen generator (oxygen source). The oxygen source accompanies the patient wherever the patient may go, including when the patient is being moved with a wheelchair. A modest-diameter, flexible, medical grade plastic tube is connected to an output port of the oxygen source, for conveying oxygen gas to the patient. The oxygen tube is connected to a nasal cannula which is inserted into the patient's nostril(s) to deliver the oxygen for inhalation by the patient. The oxygen source, particularly if it is a portable oxygen generator, typically has a handle thereon. Oxygen tanks are sometimes placed upon a small platform or bracket on the wheelchair frame. The housing or case for a portable oxygen generator often is provided with a strap for facilitating the carrying and movement of the generator. Tanks may also be fitted with a strap. The strap can be draped over the handles of a wheelchair to suspend the oxygen source from the wheelchair handles, behind the seated patient.

Thus often, when a patient requiring oxygen is being transported via wheelchair, the oxygen source is suspended from the main, rearwardly extending, handles of the wheelchair. Under such circumstances, it is common that the caregiver places or wraps the oxygen source's carry strap over and/or around the two main handles. Similarly, the patient's oxygen tube, if of sufficient length, may also be draped or wrapped over or around one or both of the chair's main handles. These acts of draping and wrapping are convenient for the caregiver, as the weight of the oxygen generator is borne by the main handles, rather than the caregiver, and the strap and tube are somewhat managed.

However, when the wheelchair main handles are not provided with any handle grips, or more commonly when they are provided with ordinary known types of handle grips, the strap for the oxygen source and the oxygen tube(s) are vulnerable to sliding off the rear free ends of the main handles. The strap, and/or the tubes, can slide side-to-side on the main handles, unwrap from a stored position, or more undesirably, slip backward toward or off the ends of the handles. The strap of an oxygen source may also slide forward on the wheelchair handles, with the undesirable result the oxygen source may be felt by the user at his or her back—particularly through a flexible fabric or plastic backset or backrest (very common on collapsible wheelchairs). If the strap of a tank or generator source slips off either or both handles, it at a minimum may create a loud and startling noise; even worse, the oxygen source may be damaged by the impact with the floor. Furthermore, oxygen tubes and cannulas should not touch the floor; a tube or cannula that contacts the floor is unsanitary and normally must be discarded.

There is a need for specialized hand grips for use on a wheelchair, which would aid in temporarily securing oxygen source straps and oxygen tubes in place upon the main handles of a wheelchair. Against the foregoing background, the present invention was developed.

SUMMARY OF THE INVENTION

There is disclosed a hand grip specially configured for use on a main push handle of a conventional (i.e., non-motorized) wheelchair. The push handles of a wheelchair are located on the back of the wheelchair. Hand grips are installed on the distal or free ends of the push handles to make them more comfortable to push the wheelchair, and improve the caregiver's grasp upon the push handles. The apparatus according to this disclosure is a handle grip that incorporates features adapted to facilitate the reliable, yet temporary, attachment to the wheelchair push handles of the strap(s) and/or oxygen tube(s) associated with a tank or generator source for supplying therapeutic oxygen gas to a patient seated (or to be seated) in the wheelchair.

BRIEF DESCRIPTION OF THE DRAWINGS

Embodiments of the invention can be better understood with reference to the following drawings, which form part of the specification and represent preferred embodiments. The drawings are not necessarily to scale (either within a view or between views), emphasis instead being placed upon illustrating the principles of the invention. In the drawings, like reference numerals designate corresponding elements throughout the several views. In the drawings.

DISCLOSURE OF A PREFERRED EMBODIMENT

The apparatus and methods of the present disclosure have to do with releasably connecting to the push handles of a wheelchair certain equipment for supplying oxygen gas to patients that are seated (or have or will be seated) in the wheelchair. While the presently disclosed apparatus is intended primarily for use with conventional wheelchairs (particularly non-motorized wheelchairs), its potential applicability is not strictly so limited. The apparatus according to this disclosure potentially may find beneficial utility upon handles and handlebars of other devices. The apparatus fundamentally comprises a specially configured handle grip adapted to receive and hold a strap that is suspended from the handle, the strap being attached (in the contemplated use) to a portable oxygen source. The handle grip according to this disclosure preferably but optionally also features means for temporarily securing oxygen tubes upon the grip.

Figure 1:
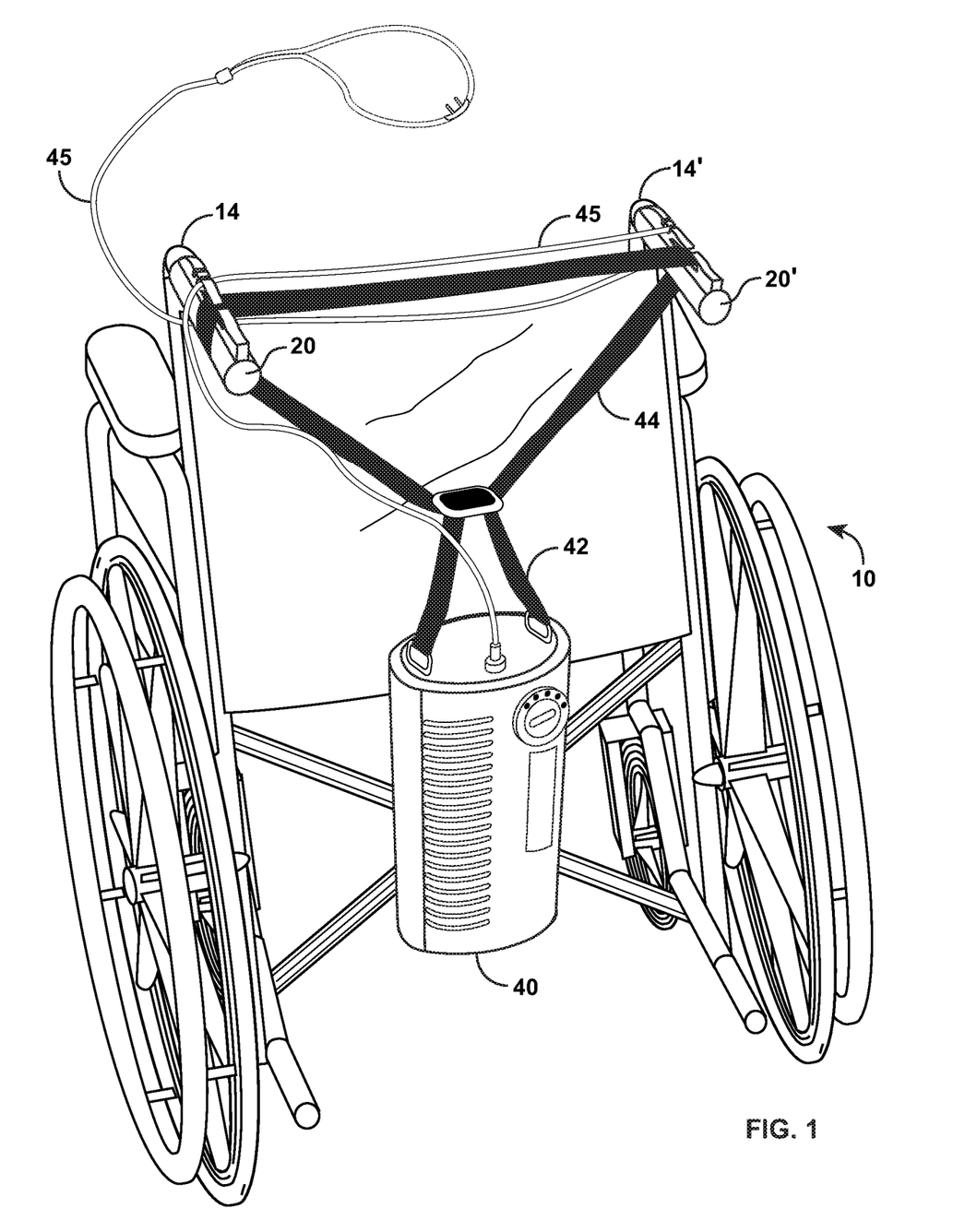
FIG. 1 is a perspective rear view of a wheelchair, with a patient seated therein, and with handle grips according to the present invention provided thereon to support an oxygen source and tubing.

Attention is first invited to FIG. 1. A conventional wheelchair 10 hereof is any wheelchair known in the art, having a frame, two main wheels, typically two front caster wheels, a seat and a backrest. Two main or push handles 14, 14' extend rearward from the top portion of the wheelchair's frame, according to convention. According to this disclosure, the innovative handle grips 20, 20' are placed upon the rear free ends of the push handles, in a manner generally well-known for handle grips. The handle grips 20, 20' are, in general overall shape, hollow cylinders such that they can be slipped over the free ends of the respective push handles 14, 14'. The handle grips 20, 20' according to this disclosure may have a secure friction fit on and around the ends of the push handles 14, 14', and/or may be reliably secured in place with a suitable adhesive.

FIG. 1 shows generally how the handle grips 20, 20' according to this disclosure are used to reliably suspend a portable oxygen source 40, (or potentially some other practical portable cargo) from the push handles 14, 14'. The source 40 may be a generator or a container. A handle strap 42, for example, may be connected to the housing or case of the source 40. The handle strap 42 itself, or a suspension strap 44 operatively associated therewith, is disposed on and around the wheelchair's push handles 14, and engaged with the handle grips 20, 20'. The mode of engagement between the grips 20, 20' and the strap 42 or 44 beneficially restrains the strap against sliding rearward off the free ends of the push handles 14, 14', or forward on the push handles towards the patient's back. Also seen in FIG. 1 is that a patient's oxygen tube 45 is wrapped upon and retained by features of the handle grips 20, 20'.

Figure 2:
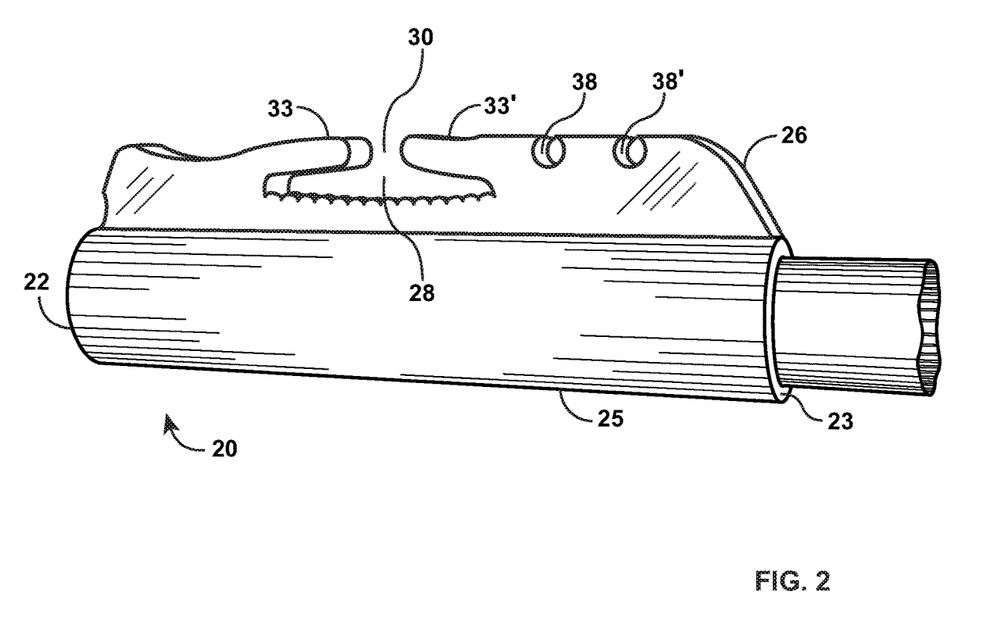
FIG. 2 is a right side view of a handle grip according to the present invention (the left side view is substantially a mirror image of the right side)
Figure 3:
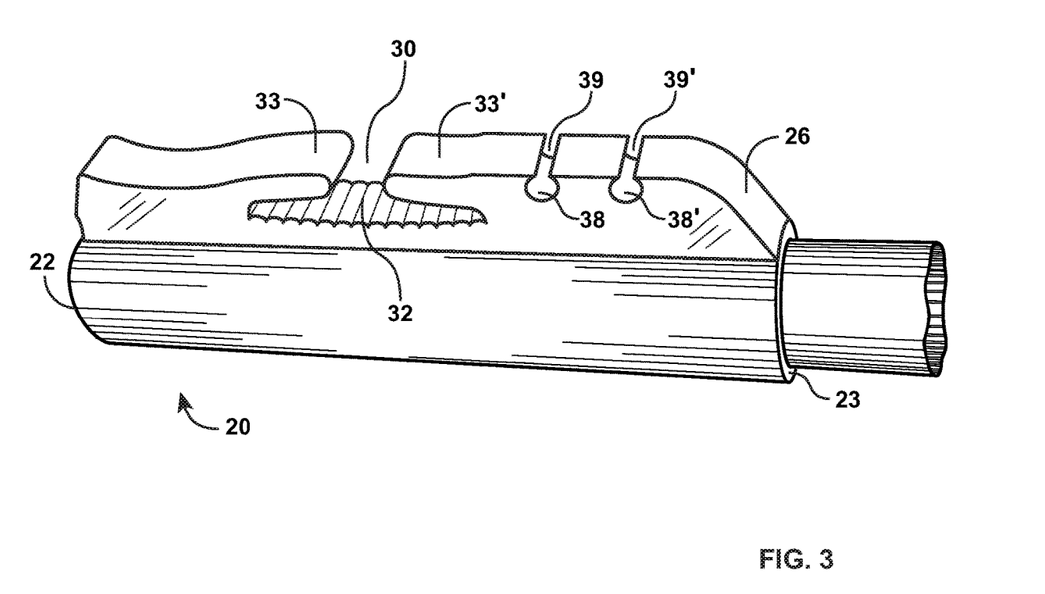
FIG. 3 is a perspective view, from above, of the right side of a handle grip according to the present invention.

Combined reference is made to FIGS. 2 and 3, showing the features and configuration of a preferred embodiment of a handle grip 20 according to the present disclosure. Description of one handle grip 20 serves to describe both grips (20 and 20') in use upon a wheelchair 10; the grip 20 may be identical in shape and form without regard for whether it is to be placed upon the left push handle 14 or the right push handle 14' of the wheelchair 10, as seen in FIG. 1.

The main body of the handle grip 20 is generally shaped as a hollow cylinder with an open proximal end 23 (into which the free end of a push handle is inserted) and a (very preferably closed or "blind") distal end 22. The grip 20 is formed or molded from a resilient plastic or polymer, many suitable compositions of which are well-known in the art. Not shown in FIGS. 2 and 3 are any finger ridges or bumps on the underside of the grip 20, which rounded ridges (typically three, or more often four, in number) are well-known in the art of handle grips for providing enhanced comfort and improved grasp. Such bumps or rounds are spaced so as to situate between the fingers of the user's hand, and at the outside of the user's fifth or "little" or "pinky" finger, while the user is grasping the handle grip. It is to be understood that the handle grip 20 according to this disclosure may be provided with such finger bumps at the appropriate and conventional locations along the surface of its hemicylindrical underside 25.

Reference is made to all the figures, particularly continued reference to FIGS. 2 and 3. The grip 20 has, upon its upper surface, an upwardly projecting rim or flange 26. The flange 26 very preferably is molded integrally with the main body of the grip, but alternatively may be a component securely adhered or welded to the top of the grip's cylindrical main body. The flange 26 is composed to be resiliently flexible, such that it can be bent and compressed in use, but when free from externally imposed pressures (such as the grasp of a user's hand) rebounds to the "rest" condition and shape. As seen in the figures, the flange 26 preferably, but not necessarily, extends along the axial length of the body of the grip 20. The height of the flange 26 (i.e., the distance it projects above the top surface of the main body) may be, for example, between about 1.5 cm and about 3.5 cm. The corners and edges of the flange 26 may be rounded and beveled to improve the comfort of a user's grasp, and to enhance aesthetic appearance.

The flange 26 defines therein a strap niche 28 as best seen in FIGS. 2 and 3. The strap niche 28, which penetrates laterally through the flange, may have any of many shapes, provided that the top opening 30 of the niche 28 is narrower/shorter (in the axial direction of the cylindrical body of the grip 20) than the bottom 32 of the niche. Thus the niche 28, broadly characterized, defines a shape in which a user folds or collapses laterally a strap (42 or 44) to then pass it though a top opening of the niche that is narrower than the niche's main vacancy, so that the strap may then be allowed to "open" to its normal width and lie within the vacancy and on a wider (in the axial direction of the grip 20) bottom of the niche.

The strap consequently is held in place against axial shifting, and is removed from the grip 20 only by deliberately reducing its dimension, so to be passed up through the narrow top opening of the niche 28. The bottom 32 of the strap niche 28 thus preferably has a length dimension (in the axial direction of the body grip 20) about equal to, or preferably modestly greater than, the lateral width of the strap (42, 44) expected to be used in cooperation with the grip 20. As seen in the figures, the aperture or vacancy of the strap niche 28 may have an abstract inverted "Y" shape; the narrow top opening 30 is defined between a pair of mutually confronting, axially extending, stiffly resilient fingers 33, 33'. The axial extent of the niche's vacancy quickly increases beneath the fingers 33, 33' till the niche extends to it maximum length at its (rounded) interior ends which are confluent into the bottom 32. As seen in FIG. 3, the niche's bottom surface 32 may be mildly corrugated to improve frictional contact with a strap (e.g. suspension strap 44 of FIG. 1) inserted into the niche 28. A suspension strap (e.g., strap 44) may be folded or laterally compressed and then passed through the narrow top opening 30, and then released/relaxed so to assume its natural width within the strap niche 28. The strap may then lie upon the bottom 32 of the niche 28, and is held against axial shifting (relative to the wheelchair's push handle 14) by the presence of the flange body 26. The fingers 33, 33' also maintain a strap on position in the niche 28; the strap can be lifted up and out of the niche 28 only by the user deliberately collapsing or folding the strap and removing it through the top opening 30.

Optionally but preferably, there also is defined in the top surface of the flange 26 at least one tube channel 38, preferably two (and optionally more than two) tube channels 38'. Each tube channel 38 extends through the flange 26 laterally, and preferably defines a cylindrical aperture with a diameter corresponding approximately to the exterior diameter of an oxygen supply tube (e.g., tube 45 in FIG. 1) to be used in cooperation with the grip 20. As depicted by the figures, the cylindrical tube channel 38 intersects the top surface of the flange 26 to create a narrow gap 39. The gap 39 has a dimension (in the axial direction of the grip 20) substantially less than the maximum diameter of the tube channel 38, so that an oxygen tube can be compressibly inserted through the gap 39 and into the channel 38. Thus disposed into the channel 38, an oxygen tube 45 is held in place in relation to the grip 20.

Figure 4:
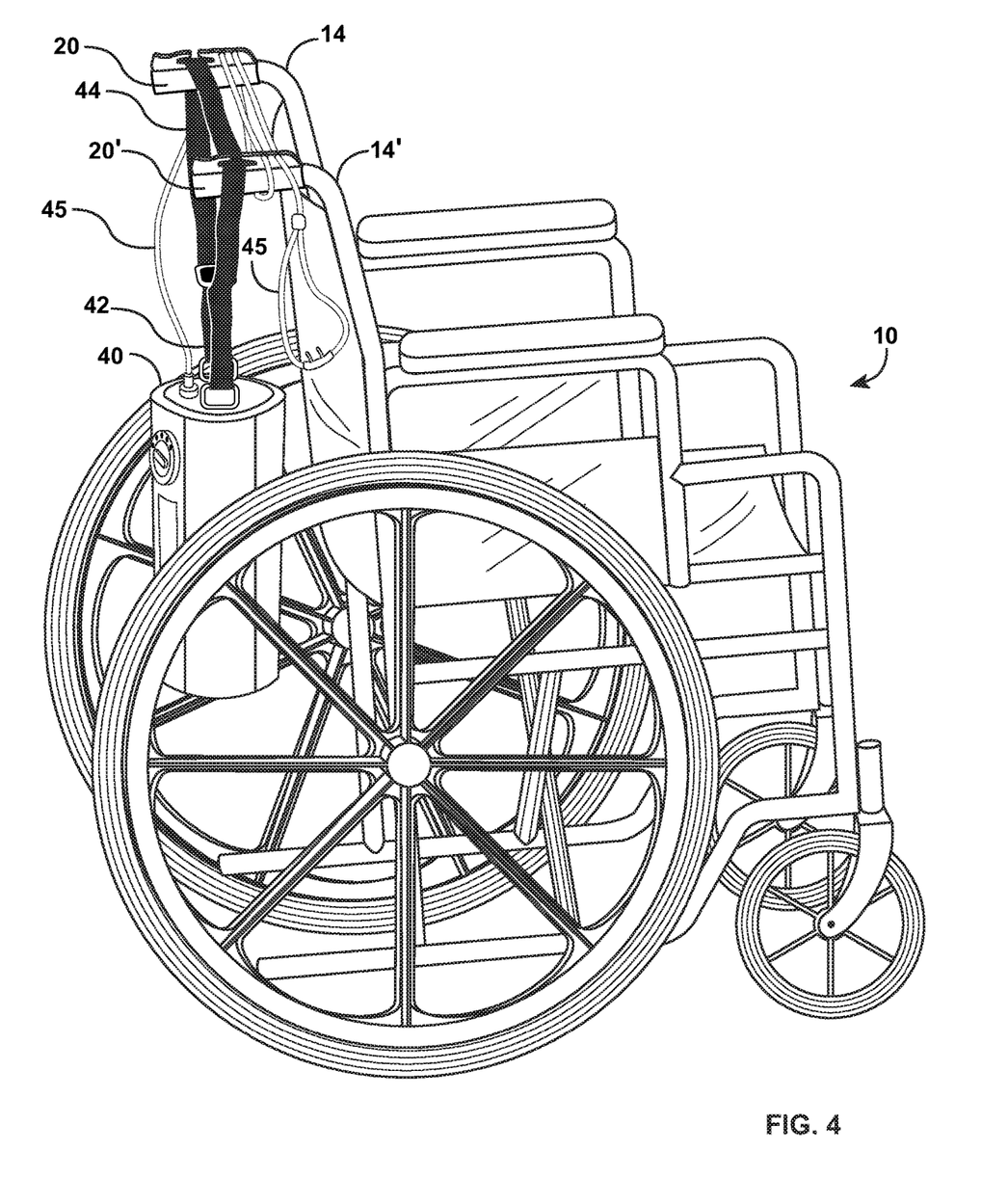
FIG. 4 is a right side diagrammatic view of a wheelchair showing handle grips according to the present invention mounted thereon, and with a strap in use to suspend from the handle grips an oxygen source, and an oxygen tube temporarily attached to the handle grips.
Figure 5:
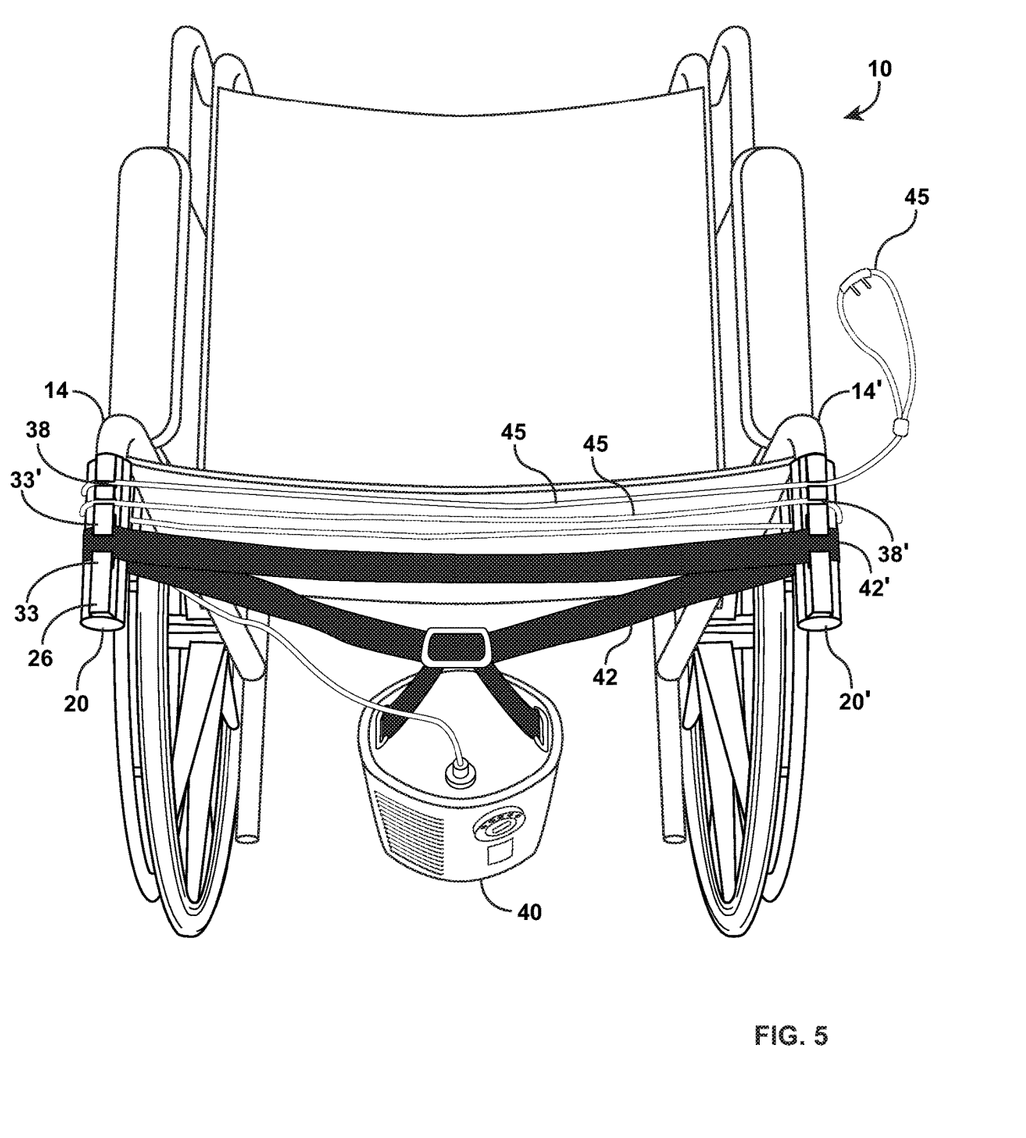
FIG. 5 is a top view of the handle grips according to the present invention, in use upon the main or push handles of a wheelchair.

The apparatus of the disclosure is seen in use in FIGS. 4 and 5. A handle grip 20 is mounted upon the distal end of each of the push handles 14, 14' of the wheelchair 10. The grips 20, 20' are oriented with their flanges 26 projecting upward, so that the strap niches 28 and the tube channels 38 are on the tops of the handle grips. When it is desired to hang an oxygen source 40 from the push handles 14, 14', a handle strap 42 (or suspension strap 44) that is connected to the source 40 is insertably engaged with the strap niche 28 of each grip 20. The strap 42 is folded or laterally compressed so to be passed through the opening 30 between the fingers 33, 33'. (The fingers 33, 33' may be mildly elastically bent to facilitate insertion of the strap through the opening 30.) The strap 42 then resumes its natural configuration and lies and is releasably confined within the niches 28 of the receptive grips 20, 20'. The strap 42 is thus maintained in place in the grips 20, 20' and upon the push handles 14, 14', and thereby releasably secured against accidental slippage along the push handles. The strap 42 accordingly is prevented from accidentally sliding toward the patient, or off of the distal ends of the push handles 14, 14' of the wheelchair 10. However, the oxygen source 40 can be removed from its suspended position by the simple expedient of manipulating the strap 42 to extract it from within the strap niches 28.

Similarly, if it is desired to releasably secure an oxygen tube 45 upon the wheelchair's push handles 14, 14', this may be done by wrapping or looping the tube around the push handles as seen in the figures, and frictionally inserting appropriate segment(s) of the tube 45 into one or more of the tube channels 38 in the tops of the grips 20, 20'. (The oxygen tube can be momentarily compressed to fit through the gap 39 of each tube channel 38; after it's emplaced in a channel 38, it elastically rebounds to its specified diameter, and is frictionally held in the channel. The tube 45 is thus releasably held in place by the grips 20, 20', and is maintained in an orderly, untangled arrangement in place upon the push handles 14, 14'. The tube(s) 45 can be removed from the grips 20, 20' by gentling pulling them up through the channel gaps 39.

Although the invention has been described in detail with reference to these preferred embodiments, other embodiments can achieve the same results. The present apparatus can be practiced by employing generally conventional materials and equipment. Accordingly, the details of such materials and equipment are not set forth herein in detail. In this description, specific details are set forth, such as specific materials, structures, processes, etc., to provide a thorough understanding of the present invention. However, as one having ordinary skill in the art would recognize, the present invention can be practiced without resorting strictly only to the details specifically set forth. In other instances, well known processing structures have not been described in detail, in order not to unnecessarily obscure the present invention.

Only some embodiments of the invention and but a few examples of its versatility are described in the present disclosure. It is understood that the invention is capable of use in various other combinations and is capable of changes or modifications within the scope of the inventive concept as expressed herein. Modifications of the invention will be obvious to those skilled in the art and it is intended to cover in the appended claims all such modifications and equivalents.

I claim:

1. A handle grip apparatus, for use upon a wheelchair handle to temporarily attach a strap or tube to the wheelchair handle, the handle being cylindrical and the grip apparatus comprising:
   a main body comprising a hollow cylinder having an axis and being closed around the full circumference of the cylinder;
   a flange projecting upward from the main body and extending along an axial length of the cylinder;
   a strap niche defined in the top of the flange and penetrating laterally through the flange, and comprising a top opening and a flat bottom;
   at least one tube channel in the top of the flange, each tube channel comprising a cylindrical aperture extending laterally through the flange; and
   wherein the top opening of the strap niche is shorter, in an axial direction of the main body, than the bottom of the niche.

2. The apparatus according to claim 1 wherein the bottom of the strap niche has a length dimension, in the axial direction of the main body, equal to or greater than a lateral width of the strap.

3. The apparatus according to claim 2 wherein the strap niche comprises a vacancy defining an inverted "T" shape.

4. The apparatus according to claim 2 wherein the top opening is defined between a pair of mutually confronting, axially extending, resilient fingers.

5. The apparatus according to claim 1 wherein the niche bottom is corrugated to improve frictional contact with the strap.

6. The apparatus according to claim 1 wherein each tube channel comprises a channel bottom that is above, relative to the axis, the bottom of the strap niche.

7. The apparatus according to claim 1 wherein the flange comprises a resiliently flexible composition which when free from externally imposed pressure rebounds to a rest shape.

8. The apparatus according to claim 1 wherein the at least one tube channel intersects a top surface of the flange to define a gap having a dimension, in the axial direction of the main body, less than a maximum diameter of the tube channel; wherein the tube is compressibly insertable through the gap and into the tube channel.

9. A handle grip apparatus, for use upon a wheelchair handle to temporarily attach a strap or tube to the wheelchair handle, the handle being cylindrical and the grip apparatus comprising:
- a closed hollow cylindrical main body having an axis, an open end and frictionally fittable on and around the wheelchair handle;
- a flange projecting upward from the main body; and
- a strap niche defined in the top of the flange and penetrating laterally through the flange and comprising a top opening and a bottom; and
- at least one tube channel in the top of the flange, each tube channel comprising:
  - a cylindrical aperture extending laterally through the flange; and
  - a channel bottom above, relative to the axis, the bottom of the strap niche; wherein the top opening of the strap niche is shorter, in the axial direction of the main body, than the bottom of the niche.

10. The apparatus according to claim 9 wherein the bottom of the strap niche is rectangular with a length dimension, in the axial direction of the main body, equal to or greater than a lateral width of the strap, wherein the strap is flat.

11. The apparatus according to claim 10 wherein the strap niche bottom is corrugated to improve frictional contact with the strap.

12. The apparatus according to claim 9 wherein the flange extends along an axial length of the main body.

13. The apparatus according to claim 12 wherein the flange comprises a resiliently flexible composition which when free from externally imposed pressure rebounds to a rest shape.

14. The apparatus according to claim 12 wherein the at least one tube channel intersects a top surface of the flange to define a gap having a dimension, in the axial direction of the main body, less than a maximum diameter of the tube channel; wherein the tube is compressibly insertable through the gap and into the tube channel.

* * * * *